United States Patent
Garcia

(10) Patent No.: US 12,016,659 B1
(45) Date of Patent: Jun. 25, 2024

(54) METHOD OF ERADICATING A BODY FROM A VIRAL INFECTION

(71) Applicant: Samuel C. Garcia, Acushnet, MA (US)

(72) Inventor: Samuel C. Garcia, Acushnet, MA (US)

( * ) Notice: Subject to any disclaimer, the term of this patent is extended or adjusted under 35 U.S.C. 154(b) by 44 days.

(21) Appl. No.: 17/658,282

(22) Filed: Apr. 7, 2022

(51) Int. Cl.
| | | |
|---|---|---|
| *A61B 5/01* | (2006.01) | |
| *A61B 5/00* | (2006.01) | |
| *A61B 5/0205* | (2006.01) | |
| *A61B 5/318* | (2021.01) | |
| *A61P 31/12* | (2006.01) | |

(52) U.S. Cl.
CPC .............. *A61B 5/01* (2013.01); *A61B 5/0008* (2013.01); *A61B 5/02055* (2013.01); *A61B 5/318* (2021.01); *A61P 31/12* (2018.01)

(58) Field of Classification Search
CPC .................................. A61P 31/14; A61M 1/16
USPC ...................................................... 340/573.1
See application file for complete search history.

(56) References Cited

U.S. PATENT DOCUMENTS

| | | | | |
|---|---|---|---|---|
| 2021/0369767 | A1* | 12/2021 | Oks | .......................... A61P 31/16 |
| 2021/0401773 | A1* | 12/2021 | Etienne | ................... A61H 33/12 |
| 2022/0031921 | A1* | 2/2022 | Vertrees | .............. A61M 1/1629 |

* cited by examiner

*Primary Examiner* — Fabricio R Murillo Garcia

(57) ABSTRACT

The present invention cures patients of viral infection completely, within hours. Through a systematic procedure, the patient will raise and maintain the ambient temperature of a room, subsequently raising their individual body temperature. The patient must remain in this heated space for a designated period of time, following the procedural steps of staying hydrated, consuming the necessary nutrients and electrolytes, showering periodically, wrapping the body in a double-layered sweat suit of some kind, and monitoring their body's temperature and response throughout. The body's reaction to viral infection is to raise its internal temperature; the present invention utilizes this natural immune system response by enhancing and intensifying it, with the goal of eliminating the virus completely.

1 Claim, 1 Drawing Sheet

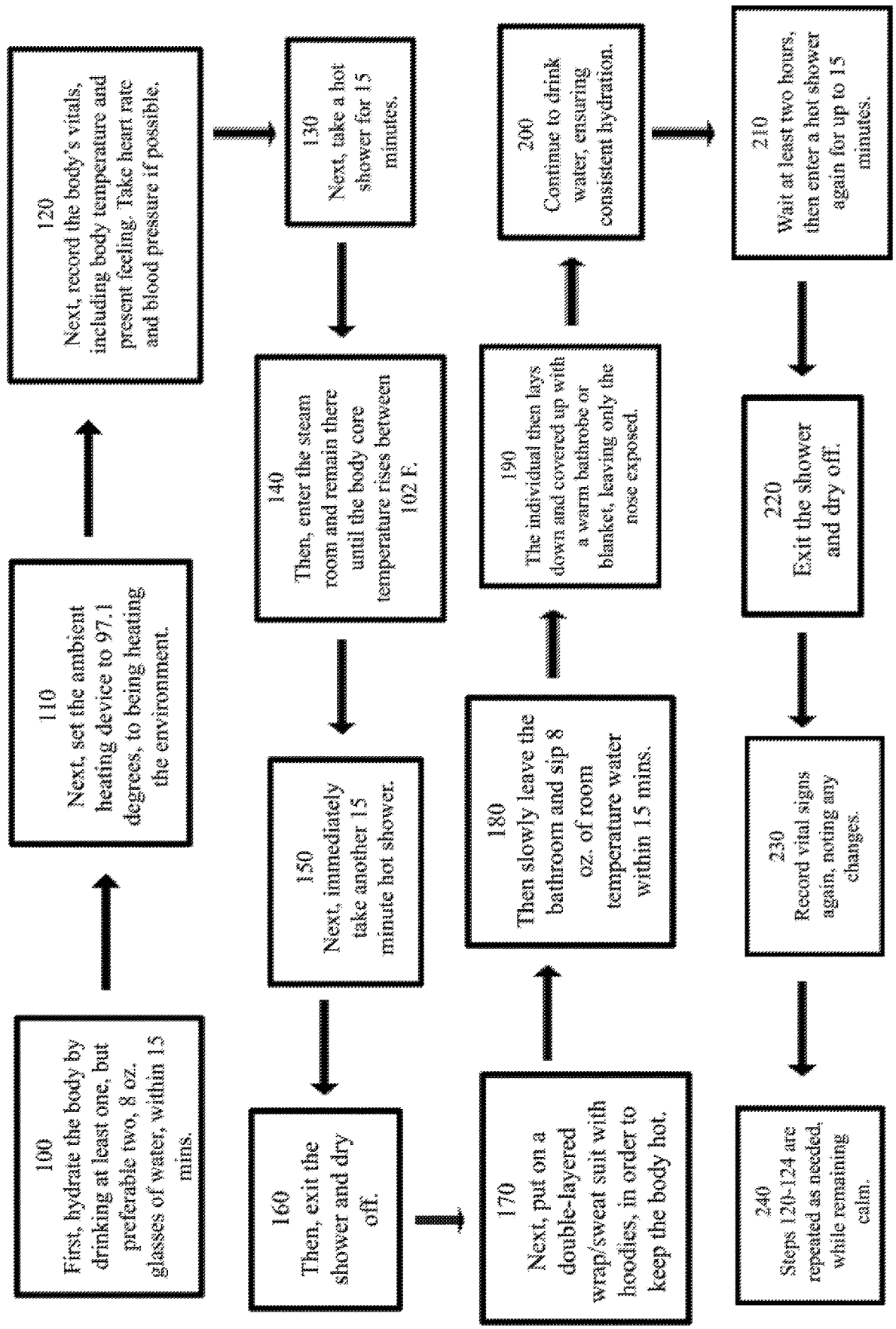

US 12,016,659 B1

METHOD OF ERADICATING A BODY FROM A VIRAL INFECTION

The present invention relates to the field of health and medicinal remedies, and more specifically relates to a method by which one may expedite the eradication of a common viral infection from one's body.

BACKGROUND OF THE INVENTION

Viral and bacterial infections are common. Thankfully, most are not life-threatening, however they certainly can put one under for a few days. With the Influenza viruses, as well as COVID-19, individuals can be put out of commission for days or even weeks, if no steps are taken to minimize the burden the virus places on the immune system.

While there are various medications available that may help to alleviate some of the symptoms of infection, few treatments are able to minimize the short term effects, shorten the time it takes to eradicate the virus from the body, or render the viral (or bacterial) infection idle in the body's systems, terminating all symptoms. If there were a simple method by which people could help their own immune system expedite the fight against the viral and bacterial contaminants in the body, people would feel better quicker, and overall suffering could be reduced.

It is well known that the human body generates a high temperature, known as a fever, when an infection is present. Generally, the higher core body temperature helps the white blood cells of the body to fight the infection(s). However, as it is generally unsafe for one to experience prolonged high fevers, they tend to taper off during certain points of the day before flaring up again. Additionally, it is generally exhausting to have a fever for a long period of time, and it tends to rapidly dehydrate the body while diminishing vital nutrients and electrolytes the body needs to continue the fight against the infection. As a higher temperature is required to expedite viral eradication in a timely manner, these periods of dehydration and recovery can impede the expediency of the healing process. If there were a method by which people could assist their body in fighting the viral load, people would heal quicker, miss less work, and ultimately suffer less.

Thus, there is a need for a new method and process by which individuals may assist their own body in the eradication of viruses and bacterial infections, including, but not limited to: the common cold, influenza, and COVID-19. Such a process preferably institutes a body-heating regimen, complete with required hydration intervals, incorporating essential nutrients, electrolytes, easily digestible foods, as to metabolically support someone sustaining a high-paced, or brisk walk. If such a process is followed precisely, the individual is assured to a quicker recovery from common viruses and bacteria.

BRIEF SUMMARY OF THE INVENTION

The present invention is a process for infection eradication configured to facilitate and expedite the recovery process of individuals who have been infected. The process employs a tiered and stepped heating method by which individuals may assist their own immune systems to ensure a more rapid recovery from common illnesses.

The following brief and detailed descriptions of the drawings are provided to explain possible embodiments of the present invention but are not provided to limit the scope of the present invention as expressed herein this summary section.

BRIEF DESCRIPTION OF SEVERAL VIEWS OF THE DRAWINGS

The accompanying drawings, which are incorporated herein and form a part of the specification, illustrate the present invention and, together with the description, further serve to explain the principles of the invention and to enable a person skilled in the pertinent art to make and use the invention.

The present invention will be better understood with reference to the appended drawing sheets, wherein:

FIG. 1 exhibits a flow chart detailing the process of the present invention.

DETAILED DESCRIPTION OF THE INVENTION

The disclosed embodiment(s) merely exemplify the invention. The scope of the invention is not limited to the disclosed embodiment(s).

References in the specification to "one embodiment," "an embodiment," "an example embodiment," etc., indicate that the embodiment described may include a particular feature, structure, or characteristic, but every embodiment may not necessarily include the particular feature, structure or characteristic. Moreover, such phrases are not necessarily referring to the same embodiment. Further, when a particular feature, structure, or characteristic is described in connection with an embodiment, it is submitted that it is within the knowledge of one skilled in the art to effect such features, structures, or characteristics in connection with other embodiments whether or not explicitly described.

The present invention is a method and process by which an individual heats his or her body to a consistent degree over a defined period of time to facilitate the elimination of the viral load of the individual, while remaining hydrated. The process includes assorted steps, to be taken in specific order, to facilitate the viral load elimination. Overall, it is important that the infected individual has a means by which he or she may raise the ambient temperature, facilitating a raise in the internal body temperature (instantly circumventing defensives) of the individual. Mechanisms by which the ambient temperature, and in turn, the individual's body temperature, may be raised include, but not are limited to: electric heaters, hot showers, hot baths, hot tubs, saunas (and respective steam rooms), electric blankets (if washable between uses), baseboard heaters, forced air heaters, heat pumps, propane heaters, fireplaces, and other conventional means of heating a room.

In an ideal execution of the present invention, a radiant heat and/or a steam room is employed to facilitate adequate elevation of the individual's body temperature. A qualified medical team may be present to monitor and assist with the overall process of the present invention. It is critical to ensure that the individual remains hydrated, and is provided with essential nutrients, as well as monitored for possible hypoxia. Pus, fluid with dead cells, the end product of the immune system, that is known to block healthy alveoli in oxygen transfer to the capillaries, should be monitored.

The process of the present invention is best outlined in the following steps, as depicted in FIG. 1:

1. First, the individual must hydrate the body, by drinking at least one, but preferably two eight-ounce glasses of water within 15 minutes. (100) This is best when the individual is not dehydrated.

2. Next, the individual sets the ambient heating device to 97.1 degrees F. (ideally, or as close as possible) to begin heating his or her environment. (110) The individual covers up his or her body with a warm bathrobe (or blankets) to help the individual maintain and increase body heat. The closer the individual gets to the temperature threshold of at least one degree over normal body core temperature, the better the results of the process will be.
3. Next, the individual records his or her vitals, including current body temperature, and present feeling (nausea, headache, tired, cramped, etc.). Additional vitals may be taken if possible, including heart rate and blood pressure. (120) If in doubt, the individual should seek medical assistance.
4. Next, the individual takes a shower. The shower should be at least 10 to 15 minutes, and the body core temperature should go up at least one, but preferably two, degree(s) over core body temperature. (130) Then, the individual enters the steam room and remains there until the body core temperature reaches no more than 102 degrees Fahrenheit. (140) Note that the temperature of the individual should not be below 99.6 degrees, or below one degree Fahrenheit over body core temperature. (if fluid is present in the lungs then dry heat may be a good option)
6. Next, the individual immediately takes a hot shower for about 10 to 15 minutes. (150). If no steam room is available, the individual should shower for 20 to 30 minutes. The core body temperature should be maintained at no more than 102 degrees Fahrenheit, and not below 99.6 degrees, or one degree Fahrenheit over body core temperature.
7. Then, the individual should exit the shower and dry off. (160)
8. Next, the individual puts on two layers: a sweat suit with a hood, a paint suit with a hood, two pairs of socks, and a scarf, giving oneself temperature consistency with the clothing needed to keep the body hot. (170) Additional clothing may be needed depending on the ambient temperature of the room. If not precisely followed, efficiency will be compromised. A bathrobe may also be used.
9. The individual then slowly leaves the bathroom and sips eight ounces of room temperature water for the next 15 minutes. (180) No cold drinks should be consumed.
10. The individual then lays down and covers up with at least two blankets, leaving just the nose of the individual exposed. (190)
11. The individual continues to drink water, ensuring consistent hydration. (200) As a precaution, do not drink to thirst.
12. The individual calmly waits at least two to three hours and then enters a hot shower again, from 15 to 25 minutes, cleansing all sweat from the body. (210)
13. The individual then exits the shower and dries off (220)
14. The individual then takes and records his or her vitals again, noting any changes. (230)
15. Steps 4-13 are then repeated while the individual remains calm and moves slowly to prevent unnecessary stress. (240)

Take note that the individual should also turn on any and all electric heaters available, assuring the consistent high temperature required for the space. The space must compliment the high temperature the individual needs over time. Additionally, the individual is instructed to close all the doors to the bathroom and make sure that any and all windows are closed.

Additionally, the individual should proceed with caution in getting the water at the spout of the shower to 102 degrees Fahrenheit. The individual must turn on the shower and gradually raise the water temperature to the highest point but avoid exceeding 108.4 during each shower. The user should not exceed an oral temperature reading of 100.7, or until he/she has exceeded his/her first oral reading by one degree and his/her armpit temperature should be 99.8 degrees. It may be lower depending on how hot the shower water was running. Do not shower for less than 10 minutes. Make sure when he or she leaves the bathroom, that he or she is completely covered and sealed from any cold air with clothing and/or cellophane plastic.

It should be understood that sweating is key and necessary in this process. Better said, the sooner the individual starts the process, the fewer hours will be needed to expel the virus. As a general rule, the treatment should be continued and repeated until becoming symptoms free within the first six hours. Then a six additional hours in bed will benefit the individual by staying warm (very warm or hot), but not with the intention of elevating the core temperature further, rather so as to relax the individual and have his/her temperature (naturally) rise while he/she sleeps. In general, any heat source can be beneficial for the present invention as long as every part of the individual's body sweats, (including the head) especially the head, and so long as the individual is not subjecting oneself to a sudden cooling down after leaving the heat source. As such, the individual should remain in the heated space until he or she begins to feel better. Even when sleeping, the room should be kept at 97.1 degrees—hot enough to deny the virus a place to harbor and easily reproduce. However, the preferred source of heat for optimal use of the present invention is a sauna or steam room. Via a steamed environment, the virus, often inhabiting the nose, becomes instantly destabilized because of the intense heat.

If a steam room or sauna is not available to the individual, he or she can actually place him/herself in a small closet with several hair dryers, however the noise of such appliances would quickly become unbearable. Showering with soap will cleanse the individual should he/she have any virus on the skin. Taking a shower is practical and effective; it can be extended for as long as you want, so long as the individual does not collapse. Ideally, the body temperature of the individual need only be raised once. With the room maintained at 97.1 degrees, the individual should remain hot all the time.

A primary infringement of the present invention is a cool room that will stop the sweating. As such, the individual should remain in the heated room until he or she begins to feel better, even when sleeping. The room needs to be at 97.1 degrees, which is hot enough to prevent the virus from having a place to harbor and reproduce easily. The Lymphatic System in combination with the immune system will complement each other to destabilize and kill the virus, driving it out along with any other contagions.

For those without electric heaters or electric blankets, individuals may be required to overdress with at least two layers of clothing, and then use cellophane or similar plastic wrap to compensate for lack of ambient heat, further covering the body, with the obvious exceptions of the mouth, eyes, and nose.

An example of the process of the present invention in action is shown below:

"COVID 19 Subject One:"

At 8:45 PM With the baseboard heater on, the individual turns on an electric heater. He or she allows the room to warm as much as possible. Ambient temperature rises to 94.9 degrees Fahrenheit.

At 9:04 PM the blood pressure on the left arm is 134 over 82, the pulse 62.

At 9:16 PM the reading on the right arm blood pressure is 123 over 65, the pulse is 64 BPM.

At 9:23 PM the running water at the spout is 102 degrees Fahrenheit. The shower running water to his/her chest is 108 degrees Fahrenheit.

9:30 PM The individual drinks three sips of water and repeats a few minutes later and again until the individual has consumed eight ounces of water within 10 or 15 minutes.

At 9:37 PM the oral temperature is 100.7 degrees Fahrenheit.

At 9:43 PM After drying, the armpit temperature is 99.8 degrees F.

Repeat this every 2 or 3 hours for at least 6 hours after having tested positive in the early stages of the infection, or until the symptoms are gone. After the first six hours, always follow with six hours of bed rest. It should be noted that the ambient temperature of the home is normally 77 degrees F.

The optimal temperature setting for ambient heaters of the home or room to increase or maintain the internal body temperature is preferably 97.1 F, because this is the temperature at which the individual requires fewer layers of clothing to maintain the internal body temperature. As COVID-19 and similar viruses are respiratory viruses, it is necessary for the incoming air to the lungs to be an aid in the destabilization of the virus. Additionally, the warmer air makes it easier to maintain the high pulse and oxygenation of the blood to accelerate repair.

Artificially raising one's core temperature will accelerate the individual's assault on the virus, bacteria, fungi, and other toxins. This is helpful as water can function similarly to that of an adhesive, which will grab everything and anything that does not belong in the individual's system. This may activate or increase the immune system's response to the virus, and ultimately its ability to detect foreign elements present that must be destroyed.

It should be understood that the ambient temperature should be high, ideally the higher the temperature one can tolerate, the better and faster the process will work. Raising one's core temperature by two to three degrees F. is ideal, however most people should only go one degree over core body temperature to be safe, or to remain in accordance with a physician care in real time. Most people in a steam room can only handle 12 minutes on average, however some can stay in for 20 minutes.

It should be further understood that the elevated body temperature must be maintained at this point via a high ambient temperature and proper clothing, which will continue to promote sweating for 2 to 3 hours at a time. This may have to be maintained for 4 to 6 hours, but if the individual is not generally in good health, it can and will become risky for them. The heartrate of the individual may be up to 114 BPM for up to 6 hours, much like an extended brisk walk. The individual will experience high heat, sweating, and some fatigue. Proper hydration is key, and not doing so will bring on symptoms of dehydration, or even heat stroke. This is why remaining calm and hydrated is so critical during this process. Being calm and in a stress-free environment is so important to the outcome of the present invention. Additionally, it should be noted that the individual should not over-drink during the present invention, but should instead maintain a proper and adequate level of hydration. Hydration should include requisite minerals, including electrolytes, to ensure proper functioning of the present invention. Electrolytes may be added to the water, or a pre-mixed electrolyte solution may be consumed by the individual.

Having illustrated the present invention, it should be understood that various adjustments and versions might be implemented without venturing away from the essence of the present invention. Further, it should be understood that the present invention is not solely limited to the invention as described in the embodiments above, but further comprises any and all embodiments within the scope of this application.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The exemplary embodiment was chosen and described in order to best explain the principles of the present invention and its practical application, to thereby enable others skilled in the art to best utilize the present invention.

The invention claimed is:

1. A method for reducing viral load in an individual infected with Covid-19, wherein the method, upon medical approval for moderate exercising or brisk walking, comprises following steps:
   a) drinking, by the individual, two eight-ounce glasses of water;
   b) setting a temperature of a recovery room to 86 F; wherein the recovery room is a room where the individual rest after taking hot showers;
   c) setting a first temperature of a recovery bathroom to 92 F; wherein the recovery bathroom is a bathroom where the individual takes the hot showers;
   d) taking three hot showers of 10 to 15 minutes each hot shower in the recovery bathroom, each hot shower taken every 3 or 4 hours;
   e) wherein for first hot shower with the first temperature of the recovery bathroom set to 92 F;
   e1) increasing individual's core temperature to 100.6 F;
   e2) after the first hot shower and while in the recovery bathroom, dressing and covering individual's body completely, including individual's head and neck;
   e3) drinking, by the individual, a first eight-ounce Glass of water;
   e4) leaving the recovery bathroom and entering to the recovery room for rest until it is time for subsequent hot showers;
   f) wherein for each of second and third hot showers with a second temperature of the recovery bathroom set to 98 F;
   f1) increasing the individual's core temperature to 99.6 F;
   f2) after the second and third hot showers and while in the recovery bathroom, dressing and covering individual's body completely, including individual's head and neck;
   f3) drinking, by the individual, a second and third eight-ounce glasses of water, respectively;
   f4) leaving the recovery bathroom and entering to the recovery room for rest: wherein after the rest after the third hot shower, taking a normal hot shower;

g) after the normal hot shower, dressing in normal clothes, drinking, by the individual, a fourth eight-ounce glass of water, and rest.

* * * * *